(12) United States Patent
Modares et al.

(10) Patent No.: US 6,654,102 B1
(45) Date of Patent: Nov. 25, 2003

(54) MINIATURE OPTICAL SENSOR

(75) Inventors: Darius Modares, Rancho Palos Verdes, CA (US); Mory Gharib, San Marino, CA (US); Fred Taugwalder, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/407,163

(22) Filed: Sep. 28, 1999

Related U.S. Application Data
(60) Provisional application No. 60/102,151, filed on Sep. 28, 1998.

(51) Int. Cl.$^7$ .................................................. G01P 3/36
(52) U.S. Cl. ......................................... 356/28.5; 356/28
(58) Field of Search ......................................... 356/28.5

(56) References Cited

U.S. PATENT DOCUMENTS

| | | | |
|---|---|---|---|
| 4,696,568 A | | 9/1987 | Weistra |
| 4,896,098 A | | 1/1990 | Haritonidis et al. |
| 4,943,157 A | * | 7/1990 | Reding |
| 5,013,928 A | | 5/1991 | Ikeda et al. |
| 5,052,228 A | | 10/1991 | Haritonidis |
| 5,187,538 A | | 2/1993 | Iwamoto et al. |
| 5,199,298 A | | 4/1993 | Ng et al. |
| 5,216,478 A | | 6/1993 | Kadowaki et al. |
| 5,465,624 A | * | 11/1995 | Tseytlin |
| 5,483,332 A | | 1/1996 | Takamiya et al. |
| 5,552,879 A | | 9/1996 | Takamiya et al. |
| 5,557,396 A | | 9/1996 | Ishizuka et al. |
| 5,557,407 A | | 9/1996 | Takamiya et al. |
| 5,587,785 A | | 12/1996 | Kato et al. |
| 5,682,236 A | | 10/1997 | Trolinger et al. |
| 5,737,070 A | | 4/1998 | Kato |

* cited by examiner

*Primary Examiner*—Stephen C. Buczinski
(74) *Attorney, Agent, or Firm*—Fish & Richardson P.C.

(57) ABSTRACT

A miniature laser Doppler probe includes a laser, lens, another lens with a diffraction grating etched thereon, and a focusing lens. The focusing lens focuses the diffraction grating on an interrogation volume which has the particles whose movement is to be detected.

15 Claims, 4 Drawing Sheets

MINIATURE OPTICAL SENSOR

CROSS REFERENCE TO RELATED APPLICATIONS

This application claims the benefit of the U.S. Provisional Application No. 60/102,151, filed on Sep. 28, 1999.

STATEMENT AS TO FEDERALLY SPONSORED RESEARCH

The invention described herein was made in the performance of work under a NASA contract, and is subject to the provisions of Public Law 96-517 (35 U.S.C. 202) in which the Contractor has elected to retain title.

BACKGROUND

Velocimeters detect velocity of moving elements. They are used in various applications. A miniature velocimeter can be used for detecting particle motion such as in industrial and medical applications. Velocimeters can also be used to detect macro motion, such as detecting the roughness of a surface, for example. Various other industrial applications are possible; such as detecting movements of belts, or the motion of a surface via its surface roughness, for example.

Laser Doppler velocimeters are commercially available. Such systems, are described, for example, in U.S. Pat. Nos. 5,557,407; 5,552,879; 5,483,332; 5,587,785; 5,013,928; 5,216,478; 5,187,538; 5,737,070; 5,199,298; 4,896,098; and 5,052,228. These generally use a gas laser and discrete optics. The instrument is large and not susceptible for easy relocation. The instruments are fragile, and typically not suitable for application in harsh environments.

Optical systems of this type have required beam alignment for the transmitting optics. Vibration and temperature changes can cause misalignment in such systems.

A diode-based laser velocimeter has been suggested. This could result in a smaller, more integrated probe.

SUMMARY

The present application describes a self aligning optical is probe with a reduced element count and a relatively small overall size. The probe can be used in environments that were not previously accessible with such a device.

In one embodiment, a laser velocimeter probe is defined that has a housing defining an interior chamber, and having first and second ends, a laser source, located in the housing and directed toward the second end, and an optical element, also located in said housing between said laser and the second end. The optical element includes at least a focusing element and a grating. A light receiver is also located in the housing, and receives scattered light from a direction of the second end.

BRIEF DESCRIPTION OF THE DRAWINGS

These and other aspects of the invention will be described in detail with reference to the accompanying drawings, wherein.

DESCRIPTION OF THE EMBODIMENTS

Figure 1A:
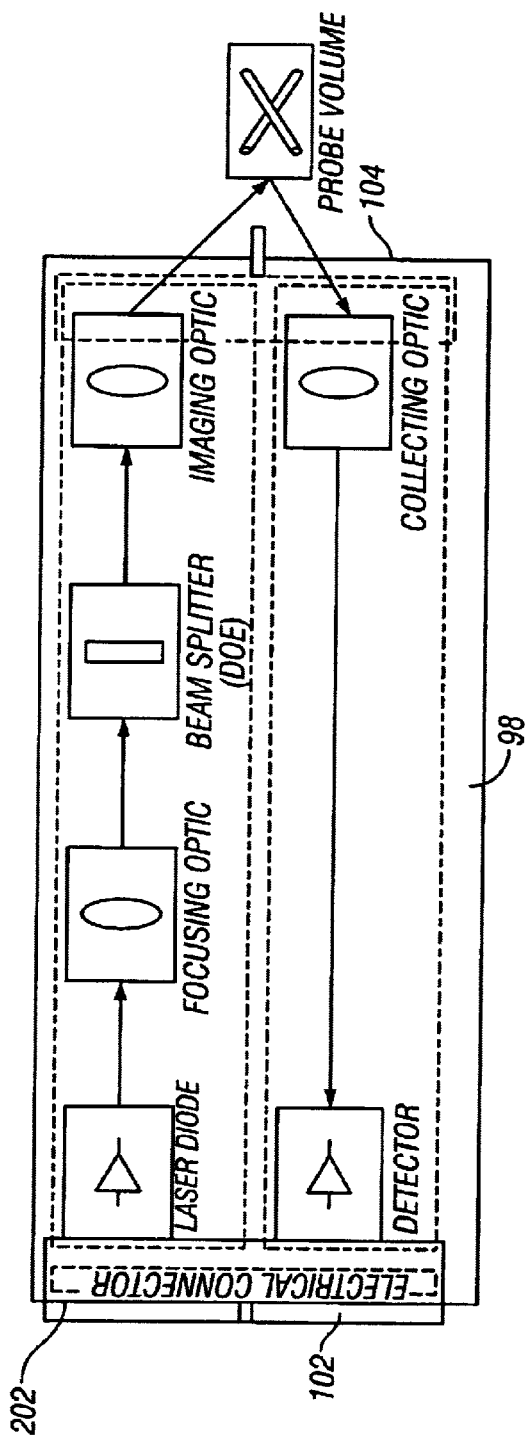
FIG. 1 shows a block diagram of the components used in the embodiment of the sensor.
FIG. 1B shows parts making up an alternative embodiment.
FIG. 1C shows scattered radiation from the probe volume directly on an optical fiber.
Figure 1C:
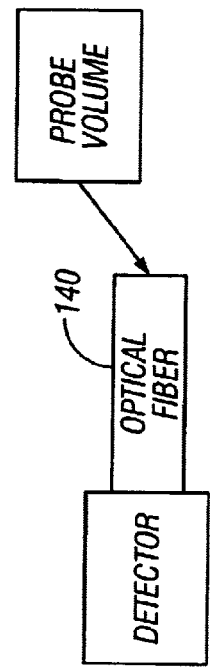
Figure 1B:
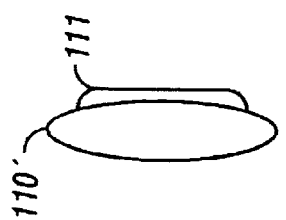
Figure 2:
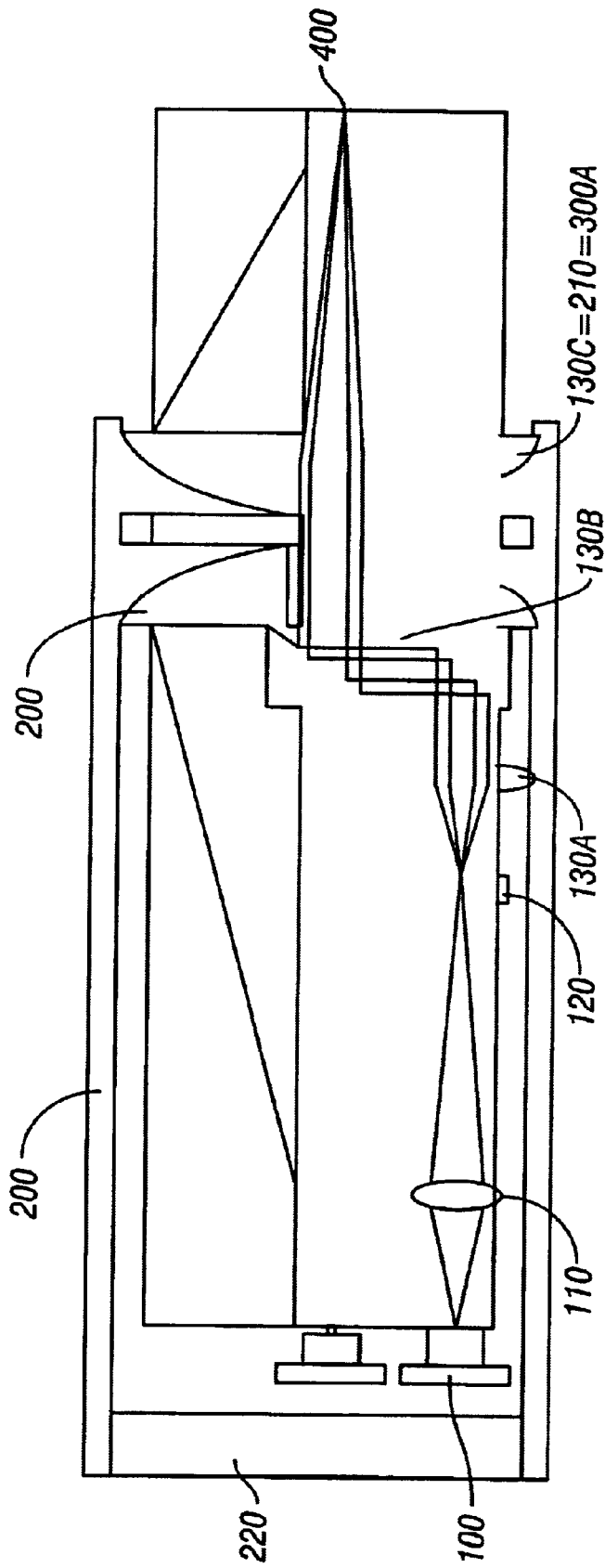
FIG. 2 shows an optical path in the actual design execution of the sensor.

FIGS. 1 and 2 show block diagrams of an embodiment.

The housing 98 in this embodiment is preferably sealed at both ends. First end 102 has a connector 202 that interfaces with wires that go in and out of the sensor. These wires carry the power and the signals indicative of the operation carried out by the sensor. A second end 104 is optically transparent, and is made out of, for example, optical glass.

A diode laser 100 produces an output laser beam which is focused on a beam splitter 120 via focusing optics, e.g. a collimating lens 110. This beam splitter 120 is a diffraction grating or more generally a Diffractive Optical Element (DOE). A second imaging optics element 130 images the fringe pattern from the diffraction grating 120 at a probe volume 400. The object to be characterized will be located at the probe volume 400.

Another embodiment shown in FIG. 1B forms the diffraction pattern on the lens itself, e.g., the diffraction pattern 111 on a surface of the lens 110'. By etching the diffraction grating on the lens itself, much of the need for the probe to be aligned is obviated.

The system uses well-known laser Doppler and anemometry techniques. The image formed at the probe volume 400 creates in space a fringe pattern. A particle or moving volume crossing this fringe pattern at the probe volume 400 will scatter light. This light coming from the probe volume is collected onto the detector 310 through the collecting optics 300.

The diode laser 100 can be any kind of small laser source at any wavelength with the correspondent optic and detector. 660 nm, 830 nm, 980 nm diodes have been successfully used.

The probe volume can be seen as an image of the diffraction grating or as the interference of two coherent light beams. The grating can define, for example, a set of parallel fringes which is focused at the measurement location. This set of fringes allows measuring the speed of moving volumes, objects or particles at the interrogation volume. Since the probe can measure diverging fringes close to the probe surface, this also measures the gradient of the velocity. Wall shear stress for example can be inferred therefrom.

The reflected laser beams are received into the collecting optics 300. Collecting optics can be a lens, or can be a receiving multimode optical fiber 140 with a numerical aperture of 0.37, and an α a of 50 µm as shown in FIG. 1C which directly receives the scattered light. This fiber is used to collect the scattered light and to transmit the collected, scattered light onto a detector.

Figure 3:
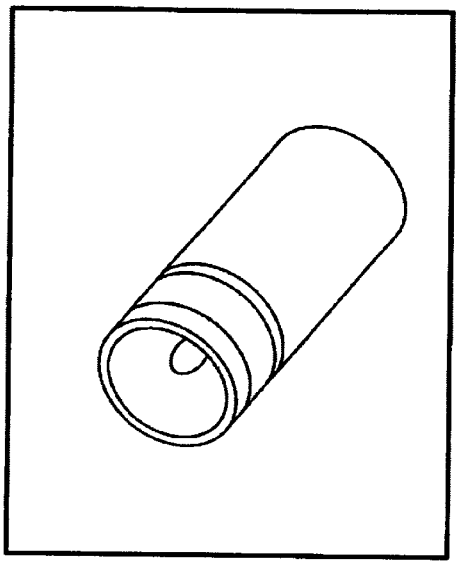
FIG. 3 shows a outside view of the sensor.

The components, e.g. laser 100, lens 110, lens/grating 120, and lens 130, are preferably attached to inside wall 98 of housing 200. Hence, this system is assembled to form a self-aligning transmitting optical system. No moving components are provided, and no individual adjustment of the beams is necessary. Also, the techniques described herein enable miniaturization of the eventual system. The unit, shown in FIG. 3, is about 1 inch in diameter.

No moving components are provided in this embodiment, and no individual adjustment of the beams is necessary. The signal to the detector is on electrical connector 202, which can connect to one or many wires that emerge from the housing. This signal is based on the scattered light of the particle or moving volume. The signal is related to the speed of the moving element, and that speed can be inferred therefrom using known techniques.

Other modifications are also possible. A first modification shown in FIG. 4 allows measuring two different velocities at the same time. This duplicates all components to form two sensors in the one housing 320 with first and second ends. The first device 300 measures a first velocity and device 310 measures a second velocity, hence simultaneously measuring both velocity components. The device has a single connector 302 commonly powering both devices 300, 310. Individual cables can return the velocity values.

Figure 4:
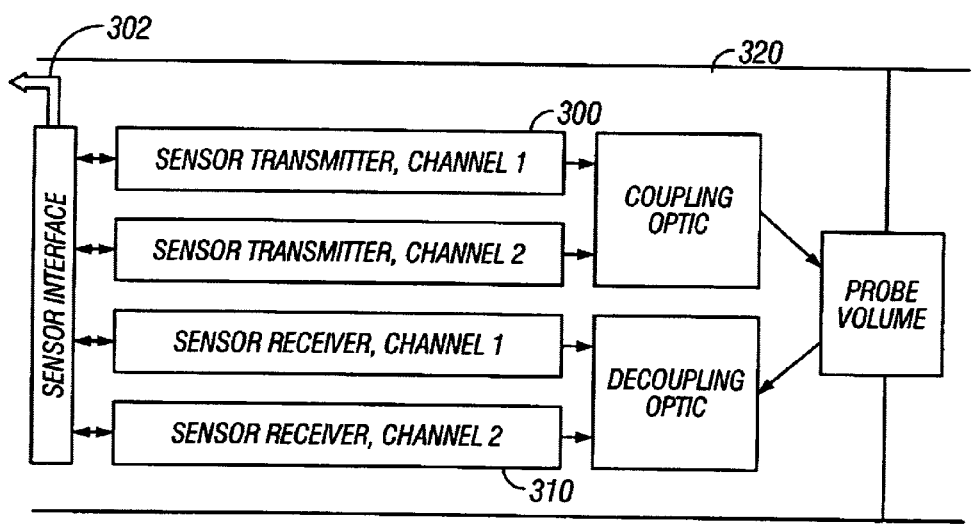
FIG. 4 shows a block diagram of a two-component sensor.

The system as shown in FIG. 4 uses a multicomponent senor where both sensors measure a common probe volume. Alternately, the probes can measure information from separate volumes.

The probe can be adapted to allow phased Doppler or Imax techniques to obtain a particle sizing probe.

Figure 5:
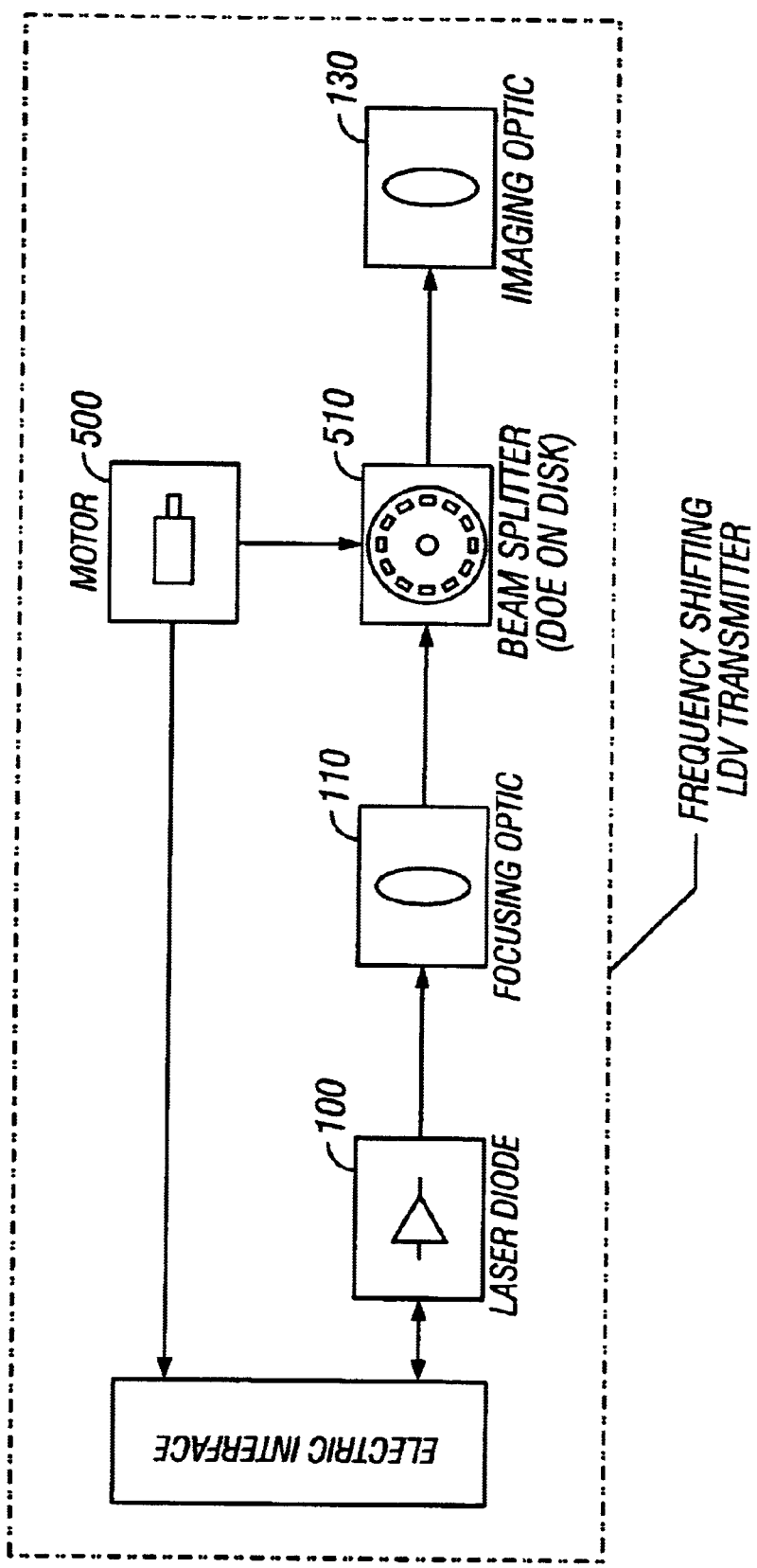
FIG. 5 shows a block diagram of a frequency-shifting sensor.

Another embodiment describes using this system in a frequency-shifted probe technique as shown in FIG. 5, which uses a rotating diffractive optical element. A rotatable grating 510 is fabricated on a rotatable disk. A rotating element, e.g. a motor 500 driven by the power supply, is coupled to rotate the diffraction grating 510. This causes a rotating fringe pattern at the area of interest. Shifts in the measured frequency caused by the rotating pattern can provide directional sensitivity.

The system described herein has been described for use in conventional velocimeter components, e.g. movement of moving objects (particle, volume, surfaces . . . ), wall shear stress measurement, and particle size measurement.

The system described herein has been described for use in conventional velocimeter components, e.g. movement of moving particles, moving macro portions, detecting surface roughness, and detecting wall shear stress. Another embodiment uses this in particle sizing. The basic design is integrated into a particle sizing probe, using well known phased Doppler and Imax techniques.

The overall optical system also minimizes the number of elements without using moving components (except for the frequency shifted probe), and without the need for beam alignment optics.

Other embodiments are within the disclosed invention.

What is claimed is:

1. A laser velocimeter probe, comprising:
    a housing defining an interior chamber and having first and second ends;
    a laser source, located in said housing and directed toward said second end;
    an optical element also located in said housing between said laser and said second end, said optical element including at least a focusing element and a grating, wherein said grating is formed on a surface of said focusing element; and
    a light receiver, also located in said housing, and receiving scattered light from a direction of said second end.

2. A probe as in claim 1 further comprising a second lens assembly coupled between said optical element and said second end, and positioned to focus laser light which has passed through said grating towards an area of said second end.

3. A probe as in claim 2 wherein an interrogation volume is defined at said second end.

4. A probe as in claim 3 wherein said second end is formed of optical glass.

5. A probe as in claim 1 wherein said laser source and said optical element are coupled to said housing to allow a constant spacing therebetween.

6. A probe as in claim 1 wherein said housing is hermetically sealed.

7. A probe as in claim 6 further comprising an optical processor processing said scattered light to determine movement information therefrom.

8. A probe as in claim 1 wherein said diffraction grating includes a set of parallel fringes.

9. A probe as in claim 1 wherein there are two of said lenses, a first of which has said diffraction grating, the other which is between said first lens with said diffraction grating and a second end, and operates to focus a view of the diffraction grating towards said second end.

10. A laser velocimeter assembly, comprising:
    a housing defining an interior chamber and having first and second ends;
    a first probe within said housing and comprising:
        a) a laser source located in said housing and directed toward said second end;
        b) an optical element also located in said housing between said laser and said second end, said optical element including at least a focusing element and a grating;
        c) a light receiver also located in said housing and receiving scattered light from a direction of said second end and using said scattered light to detect a first velocity; and
        d) an electrical connector, receiving power and providing electrical interface, said electrical connector located adjacent said first end; and
    a second probe inside said housing, located to measure a different velocity than said first velocity at a probe volume adjacent said second probe, said second probe also using said electrical connector.

11. A probe as in claim 10, wherein said housing is cylindrical, and is approximately 1 inch in diameter.

12. A self contained velocimeter probe, comprising:
    a housing having an exterior and an interior, said interior including at least one wall surface and having a first end defining a signal interfacing surface and a second end having at least a portion formed of an optically transparent material;
    a miniature laser source, coupled to said wall surface;
    a lens and diffraction grating assembly, also coupled to said wall surface and spaced from said laser source at predetermined distances to allow focusing of said laser source via said diffraction grating onto an interrogation area near said second end; and
    an optical fiber, located near said second end to receive scattered light from said interrogation area directly on the optical fiber.

13. A probe as in claim 12 wherein said optical fiber is a multimode optical fiber.

14. A method of detecting motion, comprising:
    integrating optical components including a diode, a grating and optics including a lens into a self contained housing in a self aligned manner with the grating formed directly on a surface of the lens; and
    using said optical components to detect motion.

15. A method as in claim 14, wherein said using comprises focusing light from said diode through said grating onto a volume, and receiving within said housing scattered light therefrom.

* * * * *